US008945850B2

(12) United States Patent
Claeys et al.

(10) Patent No.: US 8,945,850 B2
(45) Date of Patent: Feb. 3, 2015

(54) **DETECTION, IDENTIFICATION AND DIFFERENTIATION OF *STAPHYLOCOCCUS* USING A HYBRIDIZATION ASSAY**

(75) Inventors: Sofie Claeys, Brugge-Sint-Kruis (BE); Geert Jannes, Leuven (BE); Gerd Haberhausen, Penzberg (DE); Thomas Emrich, Iffeldorf (DE); Lia Verdoodt, De Pinte (BE)

(73) Assignees: Fujirebio Europe N.V., Ghent (BE); Roche Diagnostics GmbH, Mannheim (DE)

( * ) Notice: Subject to any disclaimer, the term of this patent is extended or adjusted under 35 U.S.C. 154(b) by 543 days.

(21) Appl. No.: 12/105,380

(22) Filed: Apr. 18, 2008

(65) Prior Publication Data

US 2008/0199878 A1 Aug. 21, 2008

Related U.S. Application Data

(63) Continuation of application No. 10/537,787, filed as application No. PCT/EP03/13907 on Dec. 8, 2003, now abandoned.

(30) Foreign Application Priority Data

Dec. 6, 2002 (EP) .................................... 02447247

(51) Int. Cl.
*C12Q 1/68* (2006.01)
*C12P 19/34* (2006.01)
*C07H 21/02* (2006.01)
*C07H 21/04* (2006.01)

(52) U.S. Cl.
CPC .................................... *C12Q 1/689* (2013.01)
USPC ....... 435/6.15; 435/6.11; 435/6.12; 435/91.2; 536/24.32; 536/24.33

(58) Field of Classification Search
None
See application file for complete search history.

(56) References Cited

U.S. PATENT DOCUMENTS

| 5,487,972 | A | * | 1/1996 | Gelfand et al. ................... 435/6 |
| 5,541,308 | A | * | 7/1996 | Hogan et al. ................. 536/23.1 |
| 5,849,488 | A |   | 12/1998 | Alatossava et al. |
| 6,025,132 | A | * | 2/2000 | Jannes et al. ...................... 435/6 |
| 6,312,903 | B1 | * | 11/2001 | Jannes et al. ...................... 435/6 |
| 6,664,064 | B1 | * | 12/2003 | Dietmaier ......................... 435/6 |
| 7,390,623 | B2 | * | 6/2008 | Jannes et al. ...................... 435/6 |
| 2006/0115819 | A1 |   | 6/2006 | Claeys et al. |

FOREIGN PATENT DOCUMENTS

EP 0 786 519 7/1997
WO WO 96/00298 1/1996

OTHER PUBLICATIONS

Gurtler NCBI GenBank Accession No. U11789 Sep. 16, 1995.
GenBank Accession No. U90017 NCBI website Dec. 9, 1997.

* cited by examiner

*Primary Examiner* — Carla Myers
(74) *Attorney, Agent, or Firm* — Nixon & Vanderhye P.C.

(57) ABSTRACT

The present invention relates to a method for the specific detection and/or identification of *Staphylococcus* species, in particular *Staphylococcus aureus*, using new nucleic acid sequences derived from the ITS (Internal Transcribed Spacer) region. The present invention relates also to said new nucleic acid sequences derived from the ITS region, between the 16S and 23S ribosomal ribonucleic acid (rRNA) or rRNA genes, to be used for the specific detection and/or identification of *Staphylococcus* species, in particular of *S. aureus*, in a biological sample. It relates also to nucleic acid primers to be used for the amplification of said spacer region of *Staphylococcus* species in a sample.

2 Claims, No Drawings

SEQUENCE LISTING

<160> NUMBER OF SEQ ID NOS: 70

<210> SEQ ID NO 1
<211> LENGTH: 143
<212> TYPE: DNA
<213> ORGANISM: staphylococcus
<220> FEATURE:
<221> NAME/KEY: misc_feature
<222> LOCATION: (141)..(141)
<223> OTHER INFORMATION: n represents a,t,c or g

<400> SEQUENCE: 1

```
tttgtacatt gaamactaga taagtaagta maatatagat tttaccargc aaaaccgagt    60
gaataaagrg ttttraayaa gcktgaattc ataasaaata atcgytagyg ttcgaragaa   120
cactcacaag wttaataack ngt                                          143
```

<210> SEQ ID NO 2
<211> LENGTH: 143
<212> TYPE: DNA
<213> ORGANISM: staphylococcus

<400> SEQUENCE: 2
tttgtacatt gaaaactaga taagtaagta aaatatagat tttaccaagc aaaaccgagt      60
gaataaagag ttttaaataa gcttgaattc ataagaaata atcgctagtg ttcgaaagaa     120
cactcacaag attaataacg cgt                                             143

<210> SEQ ID NO 3
<211> LENGTH: 63
<212> TYPE: DNA
<213> ORGANISM: staphylococcus

<400> SEQUENCE: 3
acgctcacat acggcttcgt tttcattatt ttaaatgctc atttacataa gtaaactctg      60
ctt                                                                    63

<210> SEQ ID NO 4
<211> LENGTH: 69
<212> TYPE: DNA
<213> ORGANISM: staphylococcus

<400> SEQUENCE: 4
cttatgaatt caagcttatt taaaactctt tattcactcg gttttgcttg gtaaaatcta      60
tattttact                                                              69

<210> SEQ ID NO 5
<211> LENGTH: 70
<212> TYPE: DNA
<213> ORGANISM: staphylococcus

<400> SEQUENCE: 5
cgaacactag cgattatttc ttatgaattc aagcttattt aaaactcttt attcactcgg      60
ttttgcttgg                                                             70

<210> SEQ ID NO 6
<211> LENGTH: 81
<212> TYPE: DNA
<213> ORGANISM: staphylococcus

<400> SEQUENCE: 6
ttataagtca aacgttaaca tgaagttacg ttcttttata aaaagattta aacgcgttat      60
taatcttgtg agtgttcttt c                                                81

<210> SEQ ID NO 7
<211> LENGTH: 83
<212> TYPE: DNA
<213> ORGANISM: staphylococcus

<400> SEQUENCE: 7
tataagtcaa acgctcacat acggcttcgt tttcattatt ttaaatgctc atttacataa      60
gtaaactctg ctttaaaata att                                              83

<210> SEQ ID NO 8
<211> LENGTH: 88
<212> TYPE: DNA
<213> ORGANISM: staphylococcus

<400> SEQUENCE: 8
cttatttaaa actctttatt cactcggttt tgcttggtaa aatctatatt ttacttactt      60
atctagtttt caatgtacaa ataatggt                                         88

```
<210> SEQ ID NO 9
<211> LENGTH: 88
<212> TYPE: DNA
<213> ORGANISM: staphylococcus

<400> SEQUENCE: 9
atttaaaact ctttattcac tcggttttgc ttggtaaaat ctatatttta cttacttatc    60
tagttttcaa tgtacaattt cttttttag                                      88

<210> SEQ ID NO 10
<211> LENGTH: 89
<212> TYPE: DNA
<213> ORGANISM: staphylococcus

<400> SEQUENCE: 10
gtgagtgttc tttcgaacac tagcgattat ttcttatgaa ttcaagctta tttaaaactc    60
tttattcact cggttttgct tggtaaaat                                      89

<210> SEQ ID NO 11
<211> LENGTH: 89
<212> TYPE: DNA
<213> ORGANISM: staphylococcus

<400> SEQUENCE: 11
attttaccaa gcaaaaccga gtgaataaag agttttaaat aagcttgaat tcataagaaa    60
taatcgctag tgttcgaaag aacactcac                                      89

<210> SEQ ID NO 12
<211> LENGTH: 91
<212> TYPE: DNA
<213> ORGANISM: staphylococcus

<400> SEQUENCE: 12
tttaaacgcg ttattaatct tgtgagtgtt ctttcgaaca ctagcgatta tttcttatga    60
attcaagctt atttaaaact ctttattcac t                                   91

<210> SEQ ID NO 13
<211> LENGTH: 101
<212> TYPE: DNA
<213> ORGANISM: staphylococcus

<400> SEQUENCE: 13
tccaccattt ttataagtca acgttaaca tgaagttacg ttcttttata aaaagattta     60
aacgcgttat taatcttgtg agtgttcttt cgaacactag c                       101

<210> SEQ ID NO 14
<211> LENGTH: 21
<212> TYPE: DNA
<213> ORGANISM: staphylococcus

<400> SEQUENCE: 14
agattttacc aagcaaaacc g                                              21

<210> SEQ ID NO 15
<211> LENGTH: 21
<212> TYPE: DNA
<213> ORGANISM: staphylococcus

<400> SEQUENCE: 15
agattttacc aagcaaaacc g                                              21
```

```
<210> SEQ ID NO 16
<211> LENGTH: 21
<212> TYPE: DNA
<213> ORGANISM: staphylococcus

<400> SEQUENCE: 16
aagcttgaat tcataagaaa t                                           21

<210> SEQ ID NO 17
<211> LENGTH: 23
<212> TYPE: DNA
<213> ORGANISM: staphylococcus

<400> SEQUENCE: 17
ccgagtgaat aaagagtttt aaa                                         23

<210> SEQ ID NO 18
<211> LENGTH: 24
<212> TYPE: DNA
<213> ORGANISM: staphylococcus

<400> SEQUENCE: 18
ccaagcaaaa ccgagtgaat aaag                                        24

<210> SEQ ID NO 19
<211> LENGTH: 24
<212> TYPE: DNA
<213> ORGANISM: staphylococcus

<400> SEQUENCE: 19
gcttgaattc ataagaaata atcg                                        24

<210> SEQ ID NO 20
<211> LENGTH: 25
<212> TYPE: DNA
<213> ORGANISM: staphylococcus

<400> SEQUENCE: 20
gaataaagag ttttaaataa gcttg                                       25

<210> SEQ ID NO 21
<211> LENGTH: 27
<212> TYPE: DNA
<213> ORGANISM: staphylococcus

<400> SEQUENCE: 21
gtgaataaag agttttaaat aagcttg                                     27

<210> SEQ ID NO 22
<211> LENGTH: 27
<212> TYPE: DNA
<213> ORGANISM: staphylococcus

<400> SEQUENCE: 22
aagcttgaat tcataagaaa taatcgc                                     27

<210> SEQ ID NO 23
<211> LENGTH: 28
<212> TYPE: DNA
<213> ORGANISM: staphylococcus

<400> SEQUENCE: 23
cttggtaaaa tcttacttac ttatctag                                    28
```

```
<210> SEQ ID NO 24
<211> LENGTH: 29
<212> TYPE: DNA
<213> ORGANISM: staphylococcus

<400> SEQUENCE: 24
aagcagagtt tacttatgta aatgagcat                                      29

<210> SEQ ID NO 25
<211> LENGTH: 29
<212> TYPE: DNA
<213> ORGANISM: staphylococcus

<400> SEQUENCE: 25
taccaagcaa aaccgagtga ataaagagt                                      29

<210> SEQ ID NO 26
<211> LENGTH: 29
<212> TYPE: DNA
<213> ORGANISM: staphylococcus

<400> SEQUENCE: 26
tttgtacatt gaaaactaga taagtaagt                                      29

<210> SEQ ID NO 27
<211> LENGTH: 29
<212> TYPE: DNA
<213> ORGANISM: staphylococcus

<400> SEQUENCE: 27
gcaaaaccga gtgaataaag agttttaaa                                      29

<210> SEQ ID NO 28
<211> LENGTH: 30
<212> TYPE: DNA
<213> ORGANISM: staphylococcus

<400> SEQUENCE: 28
aagcttgaat tcataagaaa taatcgctag                                     30

<210> SEQ ID NO 29
<211> LENGTH: 30
<212> TYPE: DNA
<213> ORGANISM: staphylococcus

<400> SEQUENCE: 29
agcaaaaccg agtgaataaa cagttttaaa                                     30

<210> SEQ ID NO 30
<211> LENGTH: 31
<212> TYPE: DNA
<213> ORGANISM: staphylococcus

<400> SEQUENCE: 30
attgtacatt gaaaactaga taagtaagta a                                   31

<210> SEQ ID NO 31
<211> LENGTH: 32
<212> TYPE: DNA
<213> ORGANISM: staphylococcus

<400> SEQUENCE: 31
agtgttcgaa agaacactca caagattaat aa                                  32
```

```
<210> SEQ ID NO 32
<211> LENGTH: 32
<212> TYPE: DNA
<213> ORGANISM: staphylococcus

<400> SEQUENCE: 32
agcttattta aaactcttta ttcactcggt tt                                32

<210> SEQ ID NO 33
<211> LENGTH: 33
<212> TYPE: DNA
<213> ORGANISM: staphylococcus

<400> SEQUENCE: 33
taaaataatg aaaacgaagc cgtatgtgag cgt                               33

<210> SEQ ID NO 34
<211> LENGTH: 33
<212> TYPE: DNA
<213> ORGANISM: staphylococcus

<400> SEQUENCE: 34
taaaataatg aaaacgaagc cgtatgtgag cgt                               33

<210> SEQ ID NO 35
<211> LENGTH: 33
<212> TYPE: DNA
<213> ORGANISM: staphylococcus

<400> SEQUENCE: 35
gaattcataa gaaataatcg ctagtgttcg aaa                               33

<210> SEQ ID NO 36
<211> LENGTH: 33
<212> TYPE: DNA
<213> ORGANISM: staphylococcus

<400> SEQUENCE: 36
tttcgaacac tagcgattat ttcttatgaa ttc                               33

<210> SEQ ID NO 37
<211> LENGTH: 34
<212> TYPE: DNA
<213> ORGANISM: staphylococcus

<400> SEQUENCE: 37
gcaaaaccga gtgaataaag agttttaaat aagc                              34

<210> SEQ ID NO 38
<211> LENGTH: 34
<212> TYPE: DNA
<213> ORGANISM: staphylococcus

<400> SEQUENCE: 38
gcttatttaa aactctttat tcactcggtt ttgc                              34

<210> SEQ ID NO 39
<211> LENGTH: 36
<212> TYPE: DNA
<213> ORGANISM: staphylococcus

<400> SEQUENCE: 39
gcttggtaaa atctatattt tacttactta tctagt                            36
```

```
<210> SEQ ID NO 40
<211> LENGTH: 38
<212> TYPE: DNA
<213> ORGANISM: staphylococcus

<400> SEQUENCE: 40
gtacattgaa aactagataa gtaagtaaaa tatagatt                               38

<210> SEQ ID NO 41
<211> LENGTH: 38
<212> TYPE: DNA
<213> ORGANISM: staphylococcus

<400> SEQUENCE: 41
gagttttaaa taagcttgaa ttcataagaa ataatcgc                               38

<210> SEQ ID NO 42
<211> LENGTH: 39
<212> TYPE: DNA
<213> ORGANISM: staphylococcus

<400> SEQUENCE: 42
gaaagaacac tcacaagatt aataacgcgt ttaaatctt                              39

<210> SEQ ID NO 43
<211> LENGTH: 41
<212> TYPE: DNA
<213> ORGANISM: staphylococcus

<400> SEQUENCE: 43
ttataaaaga acgtaacttc atgttaacgt ttgacttata a                           41

<210> SEQ ID NO 44
<211> LENGTH: 41
<212> TYPE: DNA
<213> ORGANISM: staphylococcus

<400> SEQUENCE: 44
ttataaaaga acgtaacttc atgttaacgt ttgacttata a                           41

<210> SEQ ID NO 45
<211> LENGTH: 17
<212> TYPE: DNA
<213> ORGANISM: staphylococcus

<400> SEQUENCE: 45
cttcagaaga tgcggaa                                                      17

<210> SEQ ID NO 46
<211> LENGTH: 18
<212> TYPE: DNA
<213> ORGANISM: staphylococcus

<400> SEQUENCE: 46
tttcgaacac tagcgatt                                                     18

<210> SEQ ID NO 47
<211> LENGTH: 21
<212> TYPE: DNA
<213> ORGANISM: staphylococcus

<400> SEQUENCE: 47
gttattaawc ttgtgagtgt t                                                 21
```

<210> SEQ ID NO 48
<211> LENGTH: 21
<212> TYPE: DNA
<213> ORGANISM: staphylococcus
<220> FEATURE:
<221> NAME/KEY: misc_feature
<222> LOCATION: (3)..(3)
<223> OTHER INFORMATION: n represents a,t,c or g

<400> SEQUENCE: 48
acnmgttatt aawcttgtga g                                         21

<210> SEQ ID NO 49
<211> LENGTH: 19
<212> TYPE: DNA
<213> ORGANISM: staphylococcus

<400> SEQUENCE: 49
cttcagaaga tgcggaata                                            19

<210> SEQ ID NO 50
<211> LENGTH: 19
<212> TYPE: DNA
<213> ORGANISM: staphylococcus

<400> SEQUENCE: 50
ttcttcagaa gatgcggaa                                            19

<210> SEQ ID NO 51
<211> LENGTH: 19
<212> TYPE: DNA
<213> ORGANISM: staphylococcus

<400> SEQUENCE: 51
ttctttcgaa cactagcga                                            19

<210> SEQ ID NO 52
<211> LENGTH: 20
<212> TYPE: DNA
<213> ORGANISM: staphylococcus

<400> SEQUENCE: 52
accaagcaaa accgagtgaa                                           20

<210> SEQ ID NO 53
<211> LENGTH: 20
<212> TYPE: DNA
<213> ORGANISM: staphylococcus

<400> SEQUENCE: 53
gttctttcga acactagcga                                           20

<210> SEQ ID NO 54
<211> LENGTH: 21
<212> TYPE: DNA
<213> ORGANISM: staphylococcus
<220> FEATURE:
<221> NAME/KEY: misc_feature
<222> LOCATION: (1)..(1)
<223> OTHER INFORMATION: n represents a,t,c or g

<400> SEQUENCE: 54
nmgttattaa wcttgtgagt g                                         21

-continued

```
<210> SEQ ID NO 55
<211> LENGTH: 20
<212> TYPE: DNA
<213> ORGANISM: staphylococcus

<400> SEQUENCE: 55
cgcgttatta atcttgtgag                                              20

<210> SEQ ID NO 56
<211> LENGTH: 20
<212> TYPE: DNA
<213> ORGANISM: staphylococcus

<400> SEQUENCE: 56
cattgaamac tagataagta                                              20

<210> SEQ ID NO 57
<211> LENGTH: 21
<212> TYPE: DNA
<213> ORGANISM: staphylococcus

<400> SEQUENCE: 57
gttattaawc ttgtgagtgt t                                            21

<210> SEQ ID NO 58
<211> LENGTH: 22
<212> TYPE: DNA
<213> ORGANISM: staphylococcus

<400> SEQUENCE: 58
acgcgttatt aatcttgtga gt                                           22

<210> SEQ ID NO 59
<211> LENGTH: 23
<212> TYPE: DNA
<213> ORGANISM: staphylococcus

<400> SEQUENCE: 59
cgaacactag cgattatttc tta                                          23

<210> SEQ ID NO 60
<211> LENGTH: 23
<212> TYPE: DNA
<213> ORGANISM: staphylococcus

<400> SEQUENCE: 60
actagcgatt atttcttatg aat                                          23

<210> SEQ ID NO 61
<211> LENGTH: 23
<212> TYPE: DNA
<213> ORGANISM: staphylococcus

<400> SEQUENCE: 61
catattgtat tcagttttga atg                                          23

<210> SEQ ID NO 62
<211> LENGTH: 19
<212> TYPE: DNA
<213> ORGANISM: staphylococcus
<220> FEATURE:
<221> NAME/KEY: misc_feature
<222> LOCATION: (1)..(1)
<223> OTHER INFORMATION: n represents a,t,c or g
```

-continued

```
<400> SEQUENCE: 62
nmgttattaa wcttgtgag                                               19

<210> SEQ ID NO 63
<211> LENGTH: 24
<212> TYPE: DNA
<213> ORGANISM: staphylococcus

<400> SEQUENCE: 63
catattgtat tcagttttga atgc                                         24

<210> SEQ ID NO 64
<211> LENGTH: 24
<212> TYPE: DNA
<213> ORGANISM: staphylococcus

<400> SEQUENCE: 64
catattgtat tcagttttga atgt                                         24

<210> SEQ ID NO 65
<211> LENGTH: 25
<212> TYPE: DNA
<213> ORGANISM: staphylococcus

<400> SEQUENCE: 65
cataagaaat aatcgctagt gttcg                                        25

<210> SEQ ID NO 66
<211> LENGTH: 25
<212> TYPE: DNA
<213> ORGANISM: staphylococcus

<400> SEQUENCE: 66
gacatattgt attcagtttt gaatg                                        25

<210> SEQ ID NO 67
<211> LENGTH: 26
<212> TYPE: DNA
<213> ORGANISM: staphylococcus

<400> SEQUENCE: 67
gaaaactaga taagtaagta aaatat                                       26

<210> SEQ ID NO 68
<211> LENGTH: 26
<212> TYPE: DNA
<213> ORGANISM: staphylococcus

<400> SEQUENCE: 68
tgtacattga aaactagata agtaag                                       26

<210> SEQ ID NO 69
<211> LENGTH: 24
<212> TYPE: DNA
<213> ORGANISM: staphylococcus

<400> SEQUENCE: 69
tttgtacatt gaamactaga taag                                         24

<210> SEQ ID NO 70
<211> LENGTH: 25
<212> TYPE: DNA
<213> ORGANISM: staphylococcus
```

```
<220> FEATURE:
<221> NAME/KEY: misc_feature
<222> LOCATION: (3)..(3)
<223> OTHER INFORMATION: n represents a,t,c or g

<400> SEQUENCE: 70
acnmgttatt aawcttgtga gtgtt                                              25
```

US 8,945,850 B2

DETECTION, IDENTIFICATION AND DIFFERENTIATION OF *STAPHYLOCOCCUS* USING A HYBRIDIZATION ASSAY

This application is a continuation of application Ser. No. 10/537,797, filed Jun. 6, 2005 now abandoned, which is a U.S. national phase of International Application PCT/EP2003/013907, filed Dec. 8, 2003, which designated the U.S. and claims benefit to EP 02447247.4, filed Dec. 6, 2002, the entire contents of each of which is hereby incorporated by reference in this application.

FIELD OF THE INVENTION

The present invention relates to a method for the specific detection and/or identification of *Staphylococcus* species, in particular *Staphylococcus aureus*, using new nucleic acid sequences derived from the ITS (Internal Transcribed Spacer) region.

The present invention relates also to said new nucleic acid sequences derived from the ITS region, between the 16S and 23S ribosomal ribonucleic acid (rRNA) or rRNA genes, to be used for the specific detection and/or identification of *Staphylococcus* species, in particular of *S. aureus*, in a biological sample.

It relates also to nucleic acid primers to be used for the amplification of said spacer region of *Staphylococcus* species in a sample.

BACKGROUND OF THE INVENTION

The genus *Staphylococcus* includes currently 32 described species and 15 subspecies. From the human clinical point of view, *S. aureus* is the most important, but some coagulase-negative species are emerging pathogens especially in nosocomial infections among critical care patients.

Certain species of the *Staphylococcus* genus are more frequently isolated as etiologic agents of a variety of infections in humans. The agents of most concern are *S. aureus, S. epidermidis, S. haemolyticus, S. lugdunensis, S. warneri* and *S. saprophyticus*.

*S. schleiferi* has been considered a significant pathogen in some European countries but has only seldom been reported in the US, which demonstrates the variability of the local epidemiology of pathogens.

In veterinary medicine *S. aureus, S. intermedius* and *S. hyicus* are the most prominent pathogens

*Staphylococcus aureus* is one of the most common nosocomial pathogens. It is responsible for several diseases, ranging from superficial cutaneous abscesses to life-threatening intravascular infections. Its propensity to establish prolonged carriage among hospitalized patients and increasing resistance to antibiotics makes control of this organism within the hospital very difficult.

Knowledge of the epidemiology of *S. aureus* colonization among patients has shed new light on the potential difficulties in interrupting nosocomial transmission. Effective control of *S. aureus* within the hospital and community requires more aggressive measures that include earlier diagnosis of colonized patients, in other words, that include a step of screening.

Because *Staphylococcus* bacteraemia still increases in frequency, it is necessary and urgent to provide more rapid methods of detection and/or identification, using probes and/or primers more sensitive and more specific.

SUMMARY OF THE INVENTION

It is an object of the present invention to provide new nucleic acid sequences derived from a particular region of the ITS of *Staphylococcus* species, which can be used, for the detection and/or identification of *Staphylococcus* species, in particular of *S. aureus*.

The present invention thus provides an isolated nucleic acid molecule consisting of SEQ ID NO 1, the RNA form of said SEQ ID NO 1 wherein T is replaced by U, the complementary form of said SEQ ID NO 1, or any homologue, and the use of said nucleic acid molecule as a target for the detection and/or identification of *Staphylococcus* species.

An aspect of the present invention relates to new polynucleotides for use as probes and/or primers, which have as target a particular region of the 16S-23S rRNA spacer region of *Staphylococcus aureus*, and which allow the detection and/or identification of *Staphylococcus* species, in particular of *Staphylococcus aureus*.

The present invention thus provides an isolated nucleic acid molecule that specifically hybridizes to SEQ ID NO 1, or to the RNA form of said SEQ ID NO 1 wherein T is replaced by U, or to the complementary form of said SEQ ID NO 1, or to any homologous sequences thereof or to a fragment of at least 20 contiguous nucleotides thereof, for the detection and/or identification of *Staphylococcus* species, in particular of *Staphylococcus aureus*.

Another aspect of the present invention relates to sets of probes for the detection and/or identification of *Staphylococcus* species, in particular of *Staphylococcus aureus* in a sample.

Another aspect of the present invention concerns primers allowing specific amplification of the 16S-23S rRNA spacer region of *Staphylococcus* species, in particular of *S. aureus*.

Another object of the present invention is a composition containing any of the new sequences of the invention, or any of the new sets of probes and/or primers of the invention; or a combination thereof.

Another object of the present invention is a kit, in which said probes and/or primers are used, for the detection and/or identification *Staphylococcus* species, in particular of *Staphylococcus aureus*.

Another object of the present invention is a rapid and reliable hybridization method for detection and/or identification of *Staphylococcus* species, in particular of *Staphylococcus aureus*.

Another object of the present invention is a hybridization method based on real time PCR for detection and/or identification of *Staphylococcus* species, in particular of *Staphylococcus aureus*.

TABLE LEGENDS

Table 1: list of SEQ IDs
Table 2: primer pairs
Table 3: set of probes
Table 4: *Staphylococcus* species

DETAILED DESCRIPTION OF THE INVENTION

The following definitions serve to illustrate the terms and expressions used in the different embodiments of the present invention as set out below.

The terms "spacer" and "ITS" (Internal Transcribed Spacer) are abbreviated terms both referring to the region between the 16S and 23S rRNA or between the 16S and 23S rRNA genes.

The term "probe" refers to single stranded oligonucleotides or polynucleotides which have a sequence which is sufficiently complementary to hybridize to the target sequence to be detected.

Preferably the probes of the invention are 70%, 80%, 90%, or more than 95% homologous to the exact complement of the target sequence to be detected. These target sequences are either genomic DNA or precursor RNA, or amplified versions thereof.

The probes of the invention can be formed by cloning of recombinant plasmids containing inserts including the corresponding nucleotide sequences, if need be by cleaving the latter out from the cloned plasmids upon using the adequate nucleases and recovering them, e.g. by fractionation according to molecular weight.

The probes according to the present invention can also be synthesized chemically, for instance by the conventional phospho-triester method.

The term "complementary" nucleic acids as used herein means that the nucleic acid sequences can form a perfect base-paired double helix with each other.

The terms "polylnucleic acid", "nucleic acid", and "polynucleotide" correspond to either double-stranded or single-stranded cDNA or genomic DNA or RNA, containing at least 5, 10, 20, 30, 40 or 50 contiguous nucleotides. A polynucleic acid which is smaller than 100 nucleotides in length is referred to as an "oligonucleotide".

They can also refer to modified nucleotides such as inosine or nucleotides containing modified groups which do not essentially alter their hybridization characteristics.

Single stranded polynucleic acid sequences are always represented in the current invention from the 5' end to the 3' end.

They can be used as such, or in their complementary form, or in their RNA form wherein T is replaced by U.

The term "closest neighbor" means the taxon which is known or expected to be most closely related in terms of DNA homology and which has to be differentiated from the organism of interest.

The expression "taxon-specific hybridization" or "taxon-specific probe" means that the probe only hybridizes to the DNA or RNA from the taxon for which it was designed and not to DNA or RNA from other taxa.

The term taxon can refer to a complete genus or a subgroup within a genus, a species or even subtype within a species (subspecies, serovars, sequevars, biovars . . . ).

The term "specific amplification" or "specific primers" refers to the fact that said primers only amplify the spacer region from these organisms for which they were designed, and not from other organisms.

The term "sensitivity" refers to the number of false negatives: i.e. if 1 of the 100 strains to be detected is missed out, the test shows a sensitivity of (100−1/100)%=99%.

The term "specificity" refers to the number of false positives: i.e. if on 100 strains detected, 2 seem to belong to organisms for which the test is not designed, the specificity of the test is (100−2/100)%=98%.

The oligonucleotides or polynucleotides selected as being "preferential" show a sensitivity and specificity of more than 80%, preferably more than 90% and most preferably more than 95%.

The term "solid support" can refer to any substrate to which a polynucleotide probe can be coupled, provided that it retains its hybridization characteristics and provided that the background level of hybridization remains low. Usually the solid substrate will be a macrotiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labeled" refers to the use of labeled nucleic acids. Labeling may be carried out by the use of labeled nucleotides incorporated during the polymerization step of the amplification such as illustrated by Saiki et al. (1988) or Bej et al. (1990) or by the use of labeled primers, or by any other method known to the person skilled in the art. The nature of the label may be isotopic ($^{32}P$, $^{35}S$, etc.) or non-isotopic (biotin, digoxigenin, fluorescent dye, biotin, enzyme, etc.).

The term "signal" refers to a series of electromagnetic waves (for example fluorescence), or changes in electrical current which carry information. The signal can be directly visible, or can be made visible and/or interpretable by different means or devices.

The "sample" may be any biological material. This biological material may be taken either directly from the infected human being, or animal, or after culturing or enrichment, or from food, from the environment, etc.

Biological material may be for example expectoration of any kind, broncheolavages, blood, skin tissue, biopsies, lymphocyte blood culture material, colonies, etc. Said samples may be prepared or extracted according to any of the techniques known in the art.

The *Staphylococcus* species that are clinically relevant in the meaning of the present invention are *S. aureus, S. auricularis, S. capitis, S. caprae, S. cohnii, S. epidermidis, S. haemolyticus, S. hominis, S. lugdunensis, S. pasteuri, S. saccharolyticus, S. saprophyticus, S. schleiferi, S. simulans, S. warneri,* and *S. xylosus* (Table 4).

The ITS is already known for some *Staphylococcus* species (WO96/00298).

In further studies, the full genome sequencing of different *Staphylococcus* species has revealed that these organisms contain at least 5 ribosomal RNA operons in their genome.

In particular, within *Staphylococcus* species, *S. aureus* strains show a variety of spacer sequences even within one single isolate.

Those different ITS, more than 16 types of sequences, vary also in length in the range of 300 to 550 base pairs.

To solve the problems generated by this very high variability, the present invention provides a particular region of the ITS, identified and delimited for its great advantage of offering a unique target sequence for the detection and/or identification of all *Staphylococcus* species, and in particular of all *Staphylococcus* species clinically relevant, and more particularly of *S. aureus*.

Indeed, it has been discovered that the target sequence of the invention are found in all type of spacer of every *Staphylococcus* species, in particular of every *Staphylococcus* species that are clinically relevant.

This particular region of the ITS, also referred to as the "target region" or "target sequence", can be defined as a nucleic acid molecule consisting of SEQ ID NO 1 or SEQ ID NO 2, or as a nucleic acid molecule that is homologous to SEQ ID NO 1 or 2, their RNA form wherein T is replaced by U, or their complementary form.

This term "target sequence" covers all the homologous sequences found in the ITS of any *Staphylococcus* species, said homologous sequences are also referred to herein after as "homologues". The degree of homology is then higher than 75%, generally higher than 80%, and even higher than 90%.

In the framework of his invention, "homologues" are ten homologous sequences to SEQ ID NO 1 or 2 or to any fragment thereof, localized in the ITS region of any *Staphylococcus* species, SEQ ID NO 1 and 2 being derived from different *S. aureus* strains.

New polynucleotides for use as probes and/or primers designed from the target sequence of the invention for the detection and/or identification of *Staphylococcus* species are also an object of the invention.

In other words, an object of the invention relates to new polynucleotides for use as probes and/or primers, which hybridize with the target sequence of the invention for the detection and/or identification of *Staphylococcus* species.

In particular, an object of the invention is an isolated nucleic acid molecule that specifically hybridizes to SEQ ID NO 1 or 2, or to the RNA form of said SEQ ID NO 1 or 2 wherein T is replaced by U, or to the complementary form of said SEQ ID NO 1 or 2, or to a fragment of at least 20 contiguous nucleotides thereof, or to any of their homologues, for the detection and/or identification of *Staphylococcus* species, in particular of *S. aureus*.

Preferred polynucleotide probes are between about 5 to about 50 bases in length, more preferably from about 10 to about 25 nucleotides and are sufficiently homologous to the target sequence.

Polynucleotides of SEQ IDs NO 1 to 70 and any of their homologues may be used as probes.

Preferred probes are polynucleotides of SEQ IDs NO 14, 16 to 23, 25 to 32, 35 to 42 and homologues.

Preferred primers of the invention are single stranded DNA polynucleotides capable of acting as a point of initiation for synthesis of the target sequence of the invention. The length and the sequence of a primer of the invention must be such that they allow to prime the synthesis of the extension products.

Preferably a primer of the invention is about 5 to about 50 nucleotides long, preferably about 15 to about 25. Its specific length and sequence is to be chosen depending on the conditions used such as temperature and ionic strength.

Preferred primers of the invention amplify the target sequence. In other words, preferred primers of the invention amplify SEQ ID NO 1 or SEQ ID NO 2 and/or homologues.

Preferred primers of the invention are polynucleotides of SEQ IDs NO 51, 52, 53, 55, 58 65, 67, 68, 69, 70, and homologues.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules known in the art.

The preferred polynucleotides of the invention for use as primers or as probes are listed in Table 1.

Polynucleotides of the invention may differ in sequence from any of the polynucleotides specified in Table 1, or from any of their homologues, either by addition to or removal from any of their respective extremities of one or several nucleotides, or by changing one or more nucleotides within said sequences, or a combination of both, provided that the equivalents then obtained still hybridize with the target sequence as the corresponding unmodified polynucleotides.

Said equivalent polynucleotides share at least 75% homology, preferably more than 80%, most preferably more than 85% homology with the corresponding unmodified polynucleotides.

When using an equivalent of a polynucleotide, it may be necessary to modify the hybridization conditions to obtain the same specificity as the corresponding unmodified polynucleotide.

As a consequence, it will also be necessary to modify accordingly the sequence of other polynucleotides when the polynucleotides are to be used in a set under the same hybridization conditions. These modifications can be done according to principles known in the art, e.g. such as those described in Hames B and Higgins S (Eds): Nucleic acid hybridization. Practical approach, IRL Press, Oxford, UK, 1985.

The polynucleotides primers and/or probes of the invention may also comprise nucleotide analogues such as phosphorothioates (Matsukura et al., 1987), alkylphosphorothioates (Miller et al., 1979) or peptide nucleic acids (Nielsen et al., 1991; Nielsen et al., 1993) or may contain intercalating agents (Asseline et al., 1984), etc.

The modified primers or probes require adaptations with respect to the conditions under which they are used in order to obtain the required specificity and sensitivity. However the results of hybridization should remain essentially the same as those obtained with the unmodified polynucleotides.

The introduction of these modifications may be advantageous in order to influence some characteristics such as hybridization kinetics, reversibility of the hybrid-formation, biological stability of the polynucleotide molecules, etc.

The probes and primers of the invention are used in methods, also objects of the present invention, for the detection and/or identification of *Staphylococcus* species, in particular of *S. aureus*.

Detection and/or identification of the target sequence can be performed by using a electrophoresis method, a hybridization method or a sequencing method.

A method of the invention for the detection of one or more *Staphylococcus* species in a sample comprises the following steps:

First, and if necessary, the nucleic acids present in the sample are made available for amplification and/or hybridization.

Secondly, and also if necessary, the nucleic acids, if present are amplified with one or another target amplification system, as specified below. Usually, amplification is needed to enhance the subsequent hybridization signal. However for some samples, or for some highly sensitive signal-amplification systems, amplification might not be necessary.

Thirdly, the nucleic acids present in the sample or the resulting amplified product are contacted with probes, and hybridization is allowed to proceed.

Finally, the hybrids are detected using a convenient and compatible detection system. From the hybridization signals or patterns observed the presence or absence of one or several *Staphylococcus* species can be deduced.

The amplification system used may be more or less universal, depending on the specific application needed.

By using universal primers located in the conserved flanking regions (16S and 23S gene) of the rRNA spacer, the spacer region of most if not all organisms of eubacterial origin will be amplified.

For some applications it may be appropriate to amplify not all organisms present in the sample but one or several *Staphylococcus* species. This may be achieved using specific primers located in the target region of *Staphylococcus* species, and for example the polynucleotides of SEQ IDs NO 69 and 70 or their homologues may be used as such a primer pair, or preferably the polynucleotides of SEQ IDs NO 58 and 68 or their homologues.

In particular, a method of the invention for detection and/or identification of *Staphylococcus* species, notably of *Staphylococcus aureus*, in a sample comprises the steps of:

(i) if need be releasing isolating and/or concentrating the polynucleic acids in the sample;

(ii) if need be amplifying the 16S-23S rRNA spacer region, or a fragment comprising the target sequence, or the target sequence or a fragment thereof, with at least one suitable primer pair;

(iii) hybridizing the polynucleic acids of step (i) or (i) with at least one polynucleotide probe that hybridizes to the target sequence, wherein the target sequence consists of SEQ ID NO 1 or 2 or homologues thereof, or to their RNA form wherein T is replaced by U, or to their complementary form, or a to a fragment of at least 20 contiguous nucleotides thereof, (iv) detecting the hybrids formed, and (v) interpreting the signal(s) obtained and erring the presence of *Staphylococcus* species and/or identifying the *Staphylococcus* species in the sample.

Preferably, the probes of the inventions hybridize under conditions of high stringency.

Under high stringency conditions only complementary nucleic acid hybrids are formed. Accordingly, the stringency of the assay conditions determines the amount of complementarity needed between two nucleic acid strands forming a hybrid. Stringency is chosen to maximize the difference in stability between the hybrid formed with the target and the non-target nucleic acid.

The hybridization conditions are chosen in such a way that the signal of hybridization obtained when a polynucleotide of the invention hybridizes specifically to a target sequence, is different from the signal obtained when said polynucleotide hybridizes to a target sequence in a non-specific manner.

In practice, the different signals may be visualized for example when its intensity is two, five, ten or more times stronger with a specific hybridization to the target, as compared to non-specific hybridization to the target sequence, LiPA system for example.

The different signals may also be visualized when different peaks are drawn in a melting curve analysis, for instance when using a real time PCR method.

The fragment mentioned in the amplification or the hybridization step of any method of the invention may comprise 20 to 50, 20 to 80 or 20 to 100 contiguous nucleotides of SEQ ID NO 1 or 2 or of any homologues.

In one embodiment, a very convenient and advantageous technique for the detection of target sequences that are possibly present in the sample is the real time PCR method.

There are different formats for the detection of amplified DNA, notably TaqMan™ probes, Molecular Beacons probes, or FRET hybridization probes.

Concerning the TaqMan™ probes, a single-stranded hybridization probe is labeled with two components. When the first component, the so-called fluorescer, is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the polymerase, for example Taq Polymerase, during the elongation phase. As a result the excited fluorescent component and the quencher are spatially separated from one another and thus a fluorescence emission of the first component can be measured (EP B 0 543 942 and U.S. Pat. No. 5,210,015).

Concerning Molecular Beacons probes, the probes are also labeled with a first component and with a quencher, the labels preferably being located at different ends of an at least partially self-complementary probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

The Fluorescence Resonance Energy Transfer (FRET) hybridization probe test format is especially useful for all kinds of homogenous hybridization assays (Matthews, J. A. and Kricka, L. J., Anal Biochem 169 (1988) 125). It is characterized by two single-stranded hybridization probes which are used simultaneously and are complementary to adjacent sites of the same stand of an (amplified) target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured only when both hybridization probes bind to adjacent positions of the target molecule to be detected.

When annealed to the target sequence, the hybridization probes must be located very close to each other, in a head to tail arrangement Usually, the gap between the labeled 3' end of the first probe and the labeled 5' end or the second probe is as small as possible, and notably consists of about 0 to 25 bases, and preferably of about 1 to about 5 bases. This allows for a close vicinity of the FRET donor compound and the FRET acceptor compound, which is typically 10-100 Ångstrom.

Alternatively to monitoring the increase in fluorescence of the FRET acceptor component, it is also possible to monitor fluorescence decrease of the FRET donor component as a quantitative measurement of hybridization event.

Among all detection formats known in the art of real time PCR, the FRET-hybridization probe format has been proven to be highly sensitive, exact and reliable (WO 97/46707; WO 97/46712; WO 97/46714). Yet, the design of appropriate FRET hybridization probe sequences may sometimes be limited by the special characteristics of the target nucleic acid sequence to be detected.

As an alternative to the usage of two FRET hybridization probes, it is also possible to use a fluorescent-labeled primer and only one labeled polynucleotide probe (Benard, P. S., et al., Anal. Biochem. 255 (1998) 101-7). In this regard, it may be chosen arbitrarily, whether the primer is labeled with the FRET donor or the FRET acceptor compound.

FRET hybridization probes (also called Hybprobes or FRET-probes) can also be used for melting curve analysis (WO 97/46707; WO 97/46712; WO 97/46714). In such an assay, the target nucleic acid is amplified first in a typical PCR reaction with suitable amplification primers. The hybridization probes may already be present during the amplification reaction or be added subsequently. After completion of the PCR-reaction, the temperature of the sample is consecutively increased. Fluorescence is detected as long as the hybridization probe is bound to the target DNA. At the melting temperature, the hybridization probe is released from their target and the fluorescent signal is decreasing immediately down to the background level. This decrease is monitored with an appropriate fluorescence versus temperature-time plot such that the negative of a first derivative function can be calculated. The temperature value corresponding to the obtained maximum of such a function is then taken as the determined melting temperature of said pair of FRET hybridization probes.

Point mutations or polymorphisms within the target nucleic acid result in a less then 100% complementarity between the target nucleic acid and the FRET probes, thus resulting in a decreased melting temperature. This enables for a common detection of a pool of sequence variants by means of FRET-Hybprobe hybridization, whereas subsequently, different members of said pool may become discriminated by means of performing melting curve analysis.

Instead of FRET hybridization probes, Molecular Beacons may alternatively be used for melting curve analysis.

Upon the availability of Real-Time PCR and homogenous Real-Time PCR melting curve analysis, discrimination of certain types of species or strains became possible using either double stranded DNA binding dyes such as SybrGreen™I, or, alternatively, specifically designed hybridization probes hybridizing to different but similar target sequences.

In the first case, melting temperature of the generated double stranded PCR product has to be determined. Yet, this method has only limited applications since few differences cannot be monitored efficiently, because minor sequence variations only result in subtle melting temperature differences.

Alternatively, hybridization probes may be used in such a way that the melting temperature of the probe/target nucleic acid hybrid is being determined.

There are different real time PCR platforms such as the ABI/Prism™ equipments, and in particular the LightCycler™ apparatus, all based on the same principle consisting of measuring the light emission, continually monitoring the emission peak during the melt cycle, determining and visualizing the temperatures (melting peaks) at which the labeled probes detach from the amplification products. The melting peak data are characteristic of a particular [probe:target] sequence because mismatches between probe and target affect the kinetics of melting, producing different melting peaks for each species of interest.

The LightCycler™ platform offers many advantages and in particular a gain of time and the possible use of several different sequence-specific fluorescent probe detection systems such as hybridization probes (HybProbes), TaqMan™ probes, Molecular Beacons and biprobes (SYBR Green I).

In a preferred method of the present invention, the HybProbe system is used, consisting of two adjacent polynucleotide probes derived from the target region of the invention, in a head-to-tail orientation, spaced by a few nucleotides, generally 0 to 25, preferably about 1 to about 5. One of the probes is labeled at its 3' end by a donor dye, the other is labeled with an acceptor molecule at its 5' end, and is phosphate blocked at the 3' end (to prevent its acting as a primer). The donor dye is generally fluorescein, and the acceptor molecule generally LC Red640 or 705.

The detection of the target sequence of the invention may be achieved also by an internal labeled PCR strand and a detection probe located on the opposite strand. The signal is dependent on the spatial approximation of the dyes, and is dependent on the amount of the target.

When both probes are hybridized to their target sequence the emitted light of the donor is transmitted to the acceptor fluorophore by Fluorescence Resonance Energy Transfer (FRET), and the emitted fluorescence (640 or 705 nm) can be detected. The intensity of the emitted fluorescence increases in parallel with the target DNA, product of the amplification.

The LightCycler probes offer the advantage over the TaqMan™ probes of not requiring hydrolysis and, therefore, no additional extension of the PCR times (annealing-elongation ≤12 s). It is therefore possible to take advantage of the high-speed thermal cycling of the LightCycler, and complete the PCR program in only 45 minutes.

And the most recent generations of this real-time PCR platform are able to monitor several probes in a single reaction, allowing the detection and/or identification of different Staphylococci, at the species level and also at lower taxonomical levels.

Moreover, it has been shown that the methods designed for TaqMan technology can be easily converted to HybProbe technology with equivalent results (Haematologica vol. 85 (12) pp. 1248-1254, December 2000).

Therefore another object of the invention relates to sets of 2 polynucleotide probes, also referred to as HybProbes, both HybProbes hybridizing to the same target sequence, adjacent to each other, with no more than 25 nucleotides between said 2 HybProbes, preferably with no more than 10 nucleotides, in particular with no more than 5 nucleotides.

One of the HybProbes is labeled with an acceptor fluorophore and the other with a donor fluorophore of a fluorescence energy transfer pair such that upon hybridization of the two HybProbes with the target sequence, the donor and acceptor fluorophores are within 0 to 25 nucleotides of one another, and preferably within 0 to 5 nucleotides of one another.

For detecting and/or identifying *Staphylococcus* species, in particular *Staphylococcus* species clinically relevant a set of two polynucleotide probes may be used, said two probes hybridizing to SEQ ID NO 1 or SEQ ID NO 2, or to the RNA form of said SEQ ID NO 1 or 2 wherein T is replaced by U, or to the complementary form of said SEQ ID NO 1 or 2, or to homologues, wherein there are no more than 25 nucleotides, preferably no more than 5 nucleotides, between said two probes.

A set of probes of the invention may also consist of 3, 4, 5, 6, 7, 8, 9, 10, or more, probes, but it preferably consists of 2 to 5 probes, and more preferably of 2 or 3 probes.

The sets of probes listed in Table 3 and their homologues are preferred sets of the invention.

Sets of 2 polynucleotides, one for use as primer, the other for use as probe, may also be used, both said primer and probe hybridizing to the target sequence consisting of SEQ ID NO 1 or 2, of the RNA form of said SEQ ID NO 1 or 2 wherein T is replaced by U, of the complementary form of said SEQ ID NO 1 or 2, or of any homologues, wherein there are no more than 25 nucleotides, preferably no more than 5 nucleotides, between said primer and said probe.

The sets of at least 2 polynucleotides of the invention are used in methods for the detection and/or identification of *Staphylococcus* species, in particular of *S. aureus*.

A method of the present invention for detection and/or identification of *Staphylococcus* species in a sample, comprises the steps of:

(i) if need be releasing, isolating and/or concentrating the polynucleic acids in the sample;

(ii) amplifying the 16S-23S rRNA spacer region, or the target sequence, or a part of the spacer comprising the target sequence, or a part of the target sequence, with at least one suitable primer pair;

(iii) hybridizing the polynucleic acids with at least one set of at least two HybProbes that hybridize to the target sequence, wherein the target sequence consist of SEQ ID NO 1 or 2, or of the RNA form of said SEQ ID NO wherein T is replaced by U, or of the complementary form of said SEQ ID NO, or of any homologues, or of a fragment of at least 20 contiguous nucleotides thereof;

(iv) detecting the hybrids formed in step (iii);

(v) inferring the presence of *Staphylococcus* species, or identifying the *Staphylococcus* species in the sample from the differential hybridization signals obtained in step (iv).

For example, a primer pair used in the amplification step is any combination of a forward primer consisting of SEQ ID NO 45, 49, 50, 52, 56, 61, 63, 64, 65, 66, 67, 68 or their homologues, and a reverse primer consisting of SEQ ID NO 46, 47, 48, 51, 53, 54, 55, 57, 58, 59, 60, 62, or their homologues.

For example, a set of 2 HybProbes used in the hybridization step is any combination of 2 HybProbes chosen among polynucleotides of SEQ IDs NO 3 to 70 or their homologues, provided that the gap between said two HybProbes when hybridized to the target sequence is less than 25 nucleotides, preferably less than 5 nucleotides.

One of the advantages of the HybProbes system resides in the fact that it allows the detection of sequence variation, including mutations, polymorphisms and other variant nucleic acid species, based on the following molecular concept: one of the HybProbe is a tightly binding "anchor probe" whereas the adjacent "sensor probe" spans the region of sequence variation. During melting of the final PCR product the sequence alteration is detected as a change in the melting temperature (Tm) of the sensor probe.

For example, if the sample contains only SEQ ID NO 1, using Hybprobes that specifically hybridize to said SEQ ID NO 1 would generate a single melting peak. If there is also a homologue in the sample, using the same two HybProbes would generate two peaks, as far as there is one mismatched base which generally induces a temperature shift easily observable.

Depending on the polynucleotides selected, their Tm and the hybridization conditions, the fluorescence may be measured during the amplification step, generating then amplification curves, or after the amplification step, for a melting curve analysis generating melting curves.

Thus the signal obtained may be visualized in the form of amplification curves or in the form of melting curves, from which it is possible to infer the presence of *Staphylococcus* species, and/or to infer which one(s) of the Staphylococci are present.

In particular, a method for detection and/or identification of *Staphylococcus* species in a sample comprises also the steps of (i) if need be releasing, isolating and/or concentrating the polynucleic acids in the sample, and (ii) amplifying the target sequence, or a part of it, with a primer pair that is labeled, (iii) hybridizing the polynucleic acids with at least one HybProbe that hybridize, adjacent to said labeled primer with less than 25 nucleotides in between, to SEQ ID NO 1, or to the RNA form of said SEQ ID NO 1 wherein T is replaced by U, or to the complementary form of said SEQ ID NO 1, or to any homologues, or to a fragment of at least 20 contiguous nucleotides thereof, (iv) detecting the hybrids formed, and (v) inferring the presence of *Staphylococcus* species and/or identifying the *Staphylococcus* species in the sample from the signals obtained in step (iv).

A method of the invention using the HybProbes system, may be adapted for the detection and identification of *Staphylococcus aureus*, allowing the distinction of *S. aureus* from other species, and in particular from coagulase negative Staphylococci (CoNS).

Then, in the amplification step, suitable primers are primer pairs that specifically amplify the target sequence which consists of SEQ ID NO 1, or of the RNA form of said SEQ ID NO wherein T is replaced by U, or of the complementary form of said SEQ ID NO.

In the hybridization step, the HybProbes should hybridize specifically to SEQ ID NO 1 or 2, or to the RNA form wherein T is replaced by U, or to the complementary form.

Therefore, *S. aureus* strains can be unequivocally distinguished from all other organisms examined by melting curve analysis.

Furthermore, only CoNS give rise to melting peas; no relevant signals are obtained with non-Staphylococci or human genomic DNA.

Preferred primer pairs used in this particular example are any combinations of forward primers chosen among SEQ ID NO 68 or 69 or their homologues and reverse primers chosen among SEQ ID NO 58 or 70 or their homologues.

The sets of HybProbes listed in Table 3 or their homologues are the preferred sets of HybProbes of the invention. A more preferred set of 2 Hybprobes consists of SEQ ID NO 17 or homologues and SEQ ID NO 19 or homologues.

The set of HybProbes consisting of SEQ ID NO 17 and 19 is able to detect *S. aureus, S. epidermidis,* and *S. haemolyticus* with a high sensitivity.

Each polynucleotide listed in Table 1, corresponding to SEQ ID NO 1 to SEQ ID NO 70 and any of their homologues, may be used in any methods of the present invention as a primer and/or as a probe, alone or in combination.

A second embodiment based also on a hybridization method is the Line Probe Assay technique. The Line Probe Assay (LiPA) is a reverse hybridization format (Saiki et al., 1989) using membrane strips onto which several polynucleotide probes (including negative or positive control polynucleotides) can be conveniently applied as parallel lines.

The LiPA technique, as described by Stuyver et al. (1993) and in international application WO 94/12670, provides a rapid and user-friendly hybridization test. Results can be read within 4 h. after the start of the amplification. After amplification during which usually a non-isotopic label is incorporated in the amplified product and alkaline denaturation, the amplified product is contacted with the probes on the membrane and the hybridization is carried out for about 1 to 1.5 h. Consequently, the hybrids formed are detected by an enzymatic procedure resulting in a visual purple-brown precipitate. The LiPA format is completely compatible with commercially available scanning devices, thus rendering automatic interpretation of the results possible. All those advantages make the LiPA format liable for use in a routine setting.

The LiPA format is an advantageous tool for detection and/or identification of pathogens at the species level but also at higher or lower taxonomical levels. For instance, probe-configurations on LiPA strips can be selected in such a manner that they can detect the complete genus of *Staphylococcus* or can identify species within the genus (e.g. *Staphylococcus aureus, epidermidis*, etc) or can in some cases even detect subtypes (subspecies, serovars, sequevars, biovars, etc. whatever is clinically relevant) within a species.

The ability to simultaneously generate hybridization results with a large number of probes is another benefit of the LiPA technology. In many cases the amount of information which can be obtained by a particular combination of probes greatly outnumbers the data obtained by using single probe assays. Therefore the selection of probes on the membrane strip is of utmost importance since an optimized set of probes will generate the maximum of information possible.

These probes can be applied to membrane strips at different locations and the result is interpreted as positive if at least one of these probes is positive. Alternatively these probes can be applied as a mixture at the same location, hereby reducing the number of lines on a strip. This reduction may be convenient in order to make the strip more concise or to be able to extend the total number of probes on one strip.

Another alternative approach, in view of its practical benefits, is the synthesis of polynucleotides harboring the sequences of two or more different probes, referred to as degenerate probes, which then can be further processed and applied to the strip as one polynucleotide molecule. This approach would considerably simplify the manufacturing procedures of the LiPA-strips. For example, probes with nucleotide sequences A and B are both required to detect all strains of taxon X. In the latter alternative a probe can be synthesized having the nucleotide sequence AB. This probe will have the combined characteristics of probes A and B.

By virtue of the above-mentioned properties the LiPA system can be considered as an efficient format for a hybridization method wherein several organisms need to be detected simultaneously in a sample.

However, it should be clear that any other hybridization assay, whereby different probes are used under the same hybridization and wash conditions can be used for the above-mentioned detection and/or selection methods. For example, it may be possible to immobilize the target nucleic acid to a solid support and use mixtures of different probes, all differently labeled, resulting in a different detection signal for each of the probes hybridized to the target. And nowadays many different supports are available.

As an example, the procedure to be followed for the detection of one or more *Staphylococcus* species in a sample using the LiPA format is outlined below.

First, and if necessary, the nucleic acids present in the sample are made available for amplification and/or hybridization.

Secondly, the nucleic acids, if present are amplified with one or another target amplification system, as specified below. Usually, amplification is needed to enhance the subsequent hybridization signal.

Thirdly, eventually after a denaturation step, the nucleic acids present in the sample or the resulting amplified product are contacted with LiPA strips onto which one or more probes (for example DNA-, RNA-, degenerate or modified probes), allowing the detection of the organisms of interest, are immobilized, and hybridization is allowed to proceed.

Finally, eventually after having performed a wash step, the hybrids are detected using a convenient and compatible detection system. From the hybridization signals or patterns observed the presence or absence of one or several organisms screened for in that particular biological sample can be deduced.

The amplification system used may be more or less universal, depending on the specific application needed.

By using universal primers located in the conserved flanking regions of the rRNA spacer, i.e. in the 16S gene and the 23S gene, the spacer region of most if not all organisms of eubacteria origin will be amplified.

For some applications it may be appropriate to amplify not all organisms present in the sample but more specifically *Staphylococcus* species. This may be achieved using specific primers located in the target region of *Staphylococcus* species, for example the polynucleotides of SEQ IDs NO 69 and 70 or their homologues may be used as such a primer pair.

A method of the invention for detection and/or identification of *Staphylococcus* species in a sample, comprises the steps of:

(i) if need be releasing, isolating and/or concentrating the polynucleic acids present in the sample;

(ii) if need be amplifying the 16S-23S rRNA spacer region, or a part of it, with at least one suitable primer pair;

(iii) hybridizing the polynucleic acids with at least one probe that hybridizes to the target sequence consisting of SEQ ID NO 1 or 2, or of the RNA form of said SEQ ID NO 1 or 2 wherein T is replaced by U, or of the complementary form of said SEQ ID NO, or of any homologues, or of a fragment of at least 20 contiguous nucleotides thereof;

(iv) detecting the hybrids formed in step (iii);

(v) identification of the micro-organism(s) present in the sample from the differential hybridization signals obtained in step (iv).

The part of the ITS mentioned in the step of amplification, is a polynucleotide comprising the target sequence, or the target sequence itself, the target sequence consisting of SEQ ID NO 1 or 2, or of the RNA form of said SEQ ID NO 1 or 2 wherein T is replaced by U, or of the complementary form of said SEQ ID NO 1 or 2, or of any homologues, or of a fragment of at least 20 contiguous nucleotides thereof.

Preferentially, the present invention provides for a method as described above wherein at least 2 micro-organisms are detected simultaneously.

A set of probes as described in step (iii) comprises at least two, three, four, five, six, seven, eight nine or more probes of the invention, or equivalents thereof.

In a preferred method of the invention, set of probes as described in step (iii) comprises at least two probes.

Preferred probes are polynucleotides of SEQ ID NO 1 to 70 and their homologues.

The present invention also provides for a method as described above, wherein the probes as specified in step (iii) are combined with at least one other probe, preferentially also from the 16S-23S rRNA spacer region, enabling the simultaneous detection of is different pathogenic bacteria liable to be present in the same sample.

Preferred probes are designed for attaining optimal performance under the same hybridization conditions so that they can be used in sets for simultaneous hybridization; this highly increases the usability of these probes and results in a significant gain in time and labor.

A kit containing any of the polynucleotides of the present invention is also an object of the invention.

A kit of the invention comprise the following components:
at least one polynucleotide hybridizing to the target sequence consisting of SEQ ID NO 1 or 2, to the RNA form of said SEQ ID NO 1 or 2 wherein T is replaced by U, to the complementary form of said SEQ ID NO 1 or 2, or to any of their homologues;
a hybridization buffer, or components necessary for producing said buffer.

A preferred kit comprises
at least one set of two HybProbes hybridizing, adjacent to each other with less than 25 nucleotides, preferably less than 5 nucleotides, to the target sequence consisting of SEQ ID NO 1 or 2, to the RNA form of sad SEQ ID NO 1 or 2 wherein T is replaced by U, to the complementary form of said SEQ ID NO 1 or 2, or to any of their homologues;
a hybridization buffer, or components necessary for producing said buffer.

TABLE 1

| SEQ IDs | UseReferences | Length | Sequence |
|---|---|---|---|
| SEQ ID NO 1 | | | TTTGTACATTGAAXACTAGATAAGTAAGTAXAATATAGATTTTACCAYGCAAAACCGAGTGAATAAGYGTTTTYAAZAAGCWTGAATTCATAAVAAATAATCGZTAGZGTTCGAYAGAACACTCACAAGUTTAATAACWSGT |
| SEQ ID NO 2 | | | TTTGTACATTGAAAACTAGATAAGTAAGTAAAATATAGATTTTACCAAGCAAAACCGAGTGAATAAGAGTTTTAAATAAGCTTGAATTCATAAGAAATAATCGCTAGTGTTCGAAAGAACACTCACAAGATTAATAACGCGT |
| SEQ ID NO 3 | CO RStau6WTcompl.1b | 63 | ACGCTCACATACGGCTTCGTTTTCATTATTTTAAATGCTCATTTACATAAGTAAACTCTGCTT |
| SEQ ID NO 4 | CO WToligoHP5 | 69 | CTTATGAATTCAAGCTTATTTAAAACTCTTTATTCACTCGGTTTTGCTTGGTAAAATCTATATTTTACT |
| SEQ ID NO 5 | CO WToligoHP6 | 70 | CGAACACTAGCGATTATTTCTTATGAATTCAAGCTTATTTAAAACTCTTTATTCACTCGGTTTTGCTTGG |
| SEQ ID NO 6 | CO RSlau7WTcompl.1b | 81 | TTATAAGTCAAACGTTAACATGAAGTTACGTTCTTTTATAAAAGATTTAAACGCGTTATTAATCTTGTGAGTGTTCTTTC |
| SEQ ID NO 7 | CO RSlau6WTcompl.1a | 83 | TATAAGTCAAACGCTCACATACGGCTTCGTTTTCATTATTTTAAATGCTCATTTACATAAGTAAACTCTGCTTTAAAATAATT |
| SEQ ID NO 8 | CO RSlauHP1WTCompl.1 | 88 | CTTATTTAAAACTCTTTATTCACTCGGTTTTGCTTGGTAAAATCTATATTTTACTTACTTATCTAGTTTTCAATGTACAAATAATGGT |
| SEQ ID NO 9 | CO WToligo-StauHP4 | 88 | ATTTAAAACTCTTTATTCACTCGGTTTTGCTTGGTAAAATCTATATTTTACTTACTTATCTAGTTTTCAATGTACAATTTCTTTTTAG |
| SEQ ID NO 10 | CO RSlauHP2WTcompl.1 | 89 | GTGAGTGTTCTTTCGAACACTAGCGATTATTTCTTATGAATTCAAGCTTATTTAAAACTCTTTATTCACTCGGTTTTGCTTGGTAAAAT |
| SEQ ID NO 11 | CO RSlauHP2cWtcompl.1 | 89 | ATTTTACCAAGCAAAACCGAGTGAATAAAGAGTTTTAAATAAGCTTGAATTCATAAGAAATAATCGCTAGTGTTCGAAAGAACACTCAC |
| SEQ ID NO 12 | CO RSlauHP3WTcompl.1 | 91 | TTTAAACGCGTTATTAATCTTGTGAGTGTTCTTTCGAACACTAGCGATTATTTCTTATGAATTCAAGCTTATTTAAAACTCTTTATTCACT |
| SEQ ID NO 13 | CO RSlau7WTcompl.1a | 101 | TCCACCATTTTTATAAGTCAAACGTTAACATGAAGTTACGTTCTTTTATAAAAGATTTAAACGCGTTATTAATCTTGTGAGTGTTCTTTCGAACACTAGC |
| SEQ ID NO 14 | HP RSlaphSP-5LC6.1 | 21 | AGATTTTACCAAGCAAAACCG |
| SEQ ID NO 15 | HP RSlauHP5-3F1.1 | 21 | AGATTTTACCAAGCAAAACCG |
| SEQ ID NO 16 | HP RSlauHP6a-5LC6.1 | 21 | AAGCTTGAATTCATAAGAAAT |
| SEQ ID NO 17 | HP RSlauHP6-3F1.1 | 23 | CCGAGTGAATAAAGAGTTTTAAA |
| SEQ ID NO 18 | HP RSlauHP4a-5LC6.1 | 24 | CCAAGCAAAACCGAGTGAATAAAG |
| SEQ ID NO 19 | HP RSlauHP6b-5LC6.1 | 24 | GCTTGAATTCATAAGAAATAATCG |
| SEQ ID NO 20 | HP RSlauHP5b-5LC6.1 | 25 | GAATAAAGAGTTTTAAATAAGCTTG |
| SEQ ID NO 21 | HP RSlauHP5a-5LC6.1 | 27 | GTGAATAAAGAGTTTTAAATAAGCTTG |
| SEQ ID NO 22 | HP RSlauHP9-5LC6 | 27 | AAGCTTGAATTCATAAGAAATAATCGC |
| SEQ ID NO 23 | HP RSlepHP8.5LCR6 | 28 | CTTGGTAAAATCTTACTTACTTATCTAG |
| SEQ ID NO 24 | HP RSlau63F1.1 | 29 | AAGCAGAGTTTACTTATGTAAATGAGCAT |
| SEQ ID NO 25 | HP RSlauHP1-5LCR64.1 | 29 | TACCAAGCAAAACCGAGTGAATAAAGAGT |
| SEQ ID NO 26 | HP RSlapnSP-3F1.1 | 29 | TTTGTACATTGAAAACTAGATAAGTAAGT |
| SEQ ID NO 27 | HP RSlauHP7-3F1 | 29 | GCAAAACCGAGTGAATAAAGAGTTTTAAA |
| SEQ ID NO 28 | HP RSlauHP7a-5LCR6 | 30 | AAGCTTGAATTCATAAGAAATAATCGCTAG |
| SEQ ID NO 29 | HP RSlauHP9-3F1 | 30 | AGCAAAACCGAGTGAATAAACAGTTTTAAA |
| SEQ ID NO 30 | HP RSlauHP4-3F1.1 | 31 | ATTGTACATTGAAAACTAGATAAGTAAGTAA |

TABLE 1-continued

| SEQ IDs | UseReferences | Length | Sequence |
|---|---|---|---|
| SEQ ID NO 31 | HP RSlauHP3-LC6.1 | 32 | AGTGTTCGAAAGAACACTCACAAGATTAATAA |
| SEQ ID NO 32 | HP RSlauHP8.3F1 | 32 | AGCTTATTTAAAACTCTTTATTCACTCGGTTT |
| SEQ ID NO 33 | HP RSlau65LC6.1 | 33 | TAAAATAATGAAAACGAAGCCGTATGTGAGCGT |
| SEQ ID NO 34 | HP RSlau65LC7.1 | 33 | TAAAATAATGAAAACGAAGCCGTATGTGAGCGT |
| SEQ ID NO 35 | HP RSlauHP2-LC6.1 | 33 | GAATTCATAAGAAATAATCGCTAGTGTTCGAAA |
| SEQ ID NO 36 | HP RSlauHP2c-3F1.1 | 33 | TTTCGAACACTAGCGATTATTTCTTATGAATTC |
| SEQ ID NO 37 | HP RSlauHP2-3F1.1 | 34 | GCAAAACCGAGTGAATAAAGAGTTTTAAATAAGC |
| SEQ ID NO 38 | HP RSlauHP2c-LC6.1 | 34 | GCTTATTTAAAACTCTTTATTCACTCGGTTTTGC |
| SEQ ID NO 39 | HP RSlauHP8.5LCR6 | 36 | GCTTGGTAAAATCTATATTTTACTTACTTATCTAGT |
| SEQ ID NO 40 | HP RSlauHP1-3FL.1 | 38 | GTACATTGAAAACTAGATAAGTAAGTAAAATATAGATT |
| SEQ ID NO 41 | HP RSlauHP3-3F1.1 | 38 | GAGTTTTAAATAAGCTTGAATTCATAAGAAATAATCGC |
| SEQ ID NO 42 | HP RSlau73F1.1 | 39 | GAAAGAACACTCACAAGATTAATAACGCGTTTAAATCTT |
| SEQ ID NO 43 | HP RSlau75LC6.1 | 41 | TTATAAAAGAACGTAACTTCATGTTAACGTTTGACTTATAA |
| SEQ ID NO 44 | HP RSlau75LC7.1 | 41 | TTATAAAAGAACGTAACTTCATGTTAACGTTTGACTTATAA |
| SEQ ID NO 45 | Pr RSlauFP18.1 | 17 | CTTCAGAAGATGCGGAA |
| SEQ ID NO 46 | Pr RSlauRP22.1 | 18 | TTTCGAACACTAGCGATT |
| SEQ ID NO 47 | Pr | 20 | GTTATTAAUCTTGTGAGTGTT |
| SEQ ID NO 48 | Pr | 20 | ACSXGTTATTAAUCTTGTGAG |
| SEQ ID NO 49 | Pr RSlauFP19.1 | 19 | CTTCAGAAGATGCGGAATA |
| SEQ ID NO 50 | Pr RSlauFP20.1 | 19 | TTCTTCAGAAGATGCGGAA |
| SEQ ID NO 51 | Pr Slaoh-P26rev | 19 | TTCTTTCGAACACTAGCGA |
| SEQ ID NO 52 | Pr SlauP01 | 20 | ACCAAGCAAAACCGAGTGAA |
| SEQ ID NO 53 | Pr Slaph-P25rev | 20 | GTTCTTTCGAACACTAGCGA |
| SEQ ID NO 54 | Pr | 20 | SXGTTATTAAUCTTGTGAGTG |
| SEQ ID NO 55 | Pr SlaphP28rev | 20 | CGCGTTATTAATCTTGTGAG |
| SEQ ID NO 56 | Pr | 20 | CATTGAAXACTAGATAAGTA |
| SEQ ID NO 57 | Pr | 20 | GTTATTAAUCTTGTGAGTGTT |
| SEQ ID NO 58 | Pr SlaphP31rev | 22 | ACGCGTTATTAATCTTGTGAGT |
| SEQ ID NO 59 | Pr RslauRP21.1 | 23 | CGAACACTAGCGATTATTTCTTA |
| SEQ ID NO 60 | Pr RSlauRP23.1 | 23 | ACTAGCGATTATTTCTTATGAAT |
| SEQ ID NO 61 | Pr SlaphP34 | 23 | CATATTGTATTCAGTTTTGAATG |
| SEQ ID NO 62 | Pr | 18 | SXGTTATTAAUCTTGTGAG |
| SEQ ID NO 63 | Pr SlaphP32 | 24 | CATATTGTATTCAGTTTTGAATGC |
| SEQ ID NO 64 | Pr SlaphP33 | 24 | CATATTGTATTCAGTTTTGAATGT |
| SEQ ID NO 65 | Pr SlauP11 | 25 | CATAAGAAATAATCGCTAGTGTTCG |
| SEQ ID NO 66 | Pr Slaph-P24 | 25 | GACATATTGTATTCAGTTTTGAATG |
| SEQ ID NO 67 | Pr SlaphP29 | 26 | GAAAACTAGATAAGTAAGTAAAATAT |
| SEQ ID NO 68 | Pr SlaphP30 | 26 | TGTACATTGAAAACTAGATAAGTAAG |

TABLE 1-continued

| SEQ IDs | UseReferences | Length | Sequence |
|---|---|---|---|
| SEQ ID NO 69 | Pr | 24 | TTTGTACATTGAAXACTAGATAAG |
| SEQ ID NO 70 | Pr | 24 | ACSXGTTATTAAUCTTGTGAGTGTT |

Use is in fact preferred use as HP = HybProbe, Pr = primer, CO = complementary polynucleotides.
S = A, T, C or G
U = A or T
V = G or C
W = T or G
X = A or C
Y = A or G
Z = T or C <SEQ ID NO: 1;DNA;staphylococcus>
TTTGTACATTGAAMACTAGATAAGTAAGTAMAATATAGATTTTACCARGC
AAAACCGAGTGAATAAAGRGTTTTRAAYAAGCKTGAATTCATAASAAATA
ATCGYTAGYGTTCGARAGAACACTCACAAGWTTAATAACKNGT <SEQ ID NO: 2;DNA;staphylococcus>
TTTGTACATTGAAAACTAGATAAGTAAGTAAAATATAGATTTTACCAAGC
AAAACCGAGTGAATAAAGAGTTTTAAATAAGCTTGAATTCATAAGAAATA
ATCGCTAGTGTTCGAAAGAACACTCACAAGATTAATAACGCGT <SEQ ID NO: 3;DNA;staphylococcus>
ACGCTCACATACGGCTTCGTTTTCATTATTTTAAATGCTCATTTACATAA
GTAAACTCTGCTT <SEQ ID NO: 4;DNA;staphylococcus>
CTTATGAATTCAAGCTTATTTAAAACTCTTTATTCACTCGGTTTTGCTTG
GTAAAATCTATATTTTACT <SEQ ID NO: 5;DNA;staphylococcus>
CGAACACTAGCGATTATTTCTTATGAATTCAAGCTTATTTAAAACTCTTT
ATTCACTCGGTTTTGCTTGG <SEQ ID NO: 6;DNA;staphylococcus>
TTATAAGTCAAACGTTAACATGAAGTTACGTTCTTTTATAAAAAGATTTA
AACGCGTTATTAATCTTGTGAGTGTTCTTTC <SEQ ID NO: 7;DNA;staphylococcus>
TATAAGTCAAACGCTCACATACGGCTTCGTTTTCATTATTTTAAATGCTC
ATTTACATAAGTAAACTCTGCTTTAAAATAATT <SEQ ID NO: 8;DNA;staphylococcus>
CTTATTTAAAACTCTTTATTCACTCGGTTTTGCTTGGTAAAATCTATATT
TTACTTACTTATCTAGTTTTCAATGTACAAATAATGGT <SEQ ID NO: 9;DNA;staphylococcus>
ATTTAAAACTCTTTATTCACTCGGTTTTGCTTGGTAAAATCTATATTTTA
CTTACTTATCTAGTTTTCAATGTACAATTTCTTTTTAG <SEQ ID NO: 10;DNAstaphylococcus>
GTGAGTGTTCTTTCGAACACTAGCGATTATTTCTTATGAATTCAAGCTTA
TTTAAAACTCTTTATTCACTCGGTTTTGCTTGGTAAAAT <SEQ ID NO: 11;DNA;staphylococcus>
ATTTTACCAAGCAAAACCGAGTGAATAAAGAGTTTTAAATAAGCTTGAAT
TCATAAGAAATAATCGCTAGTGTTCGAAAGAACACTCAC <SEQ ID NO: 12;DNA;staphylococcus>
TTTAAACGCGTTATTAATCTTGTGAGTGTTCTTTCGAACACTAGCGATTA
TTTCTTATGAATTCAAGCTTATTTAAAACTCTTTATTCACT <SEQ ID NO: 13;DNA;staphylococcus>
TCCACCATTTTTATAAGTCAAACGTTAACATGAAGTTACGTTCTTTTATA
AAAGATTTAAACGCGTTATTAATCTTGTGAGTGTTCTTTCGAACACTAG
C <SEQ ID NO: 14;DNA;staphylococcus>
AGATTTTACCAAGCAAAACCG <SEQ ID NO: 15;DNA;staphylococcus>
AGATTTTACCAAGCAAAACCG <SEQ ID NO: 16;DNA;staphylococcus>
AAGCTTGAATTCATAAGAAAT <SEQ ID NO: 17;DNA;staphylococcus>
CCGAGTGAATAAAGAGTTTTAAA <SEQ ID NO: 18;DNA;staphylococcus>
CCAAGCAAAACCGAGTGAATAAAG <SEQ ID NO: 19;DNA;staphylococcus>
GCTTGAATTCATAAGAAATAATCG <SEQ ID NO: 20;DNA;staphylococcus>
GAATAAAGAGTTTTAAATAAGCTTG <SEQ ID NO: 21;DNA;staphylococcus>
GTGAATAAAGAGTTTTAAATAAGCTTG <SEQ ID NO: 22;DNA;staphylococcus>
AAGCTTGAATTCATAAGAAATAATCGC <SEQ ID NO: 23;DNA;staphylococcus>
CTTGGTAAAATCTTACTTACTTATCTAG <SEQ ID NO: 24;DNA;staphylococcus>
AAGCAGAGTTTACTTATGTAAATGAGCAT <SEQ ID NO: 25;DNA;staphylococcus>
TACCAAGCAAAACCGAGTGAATAAAGAGT <SEQ ID NO: 26;DNA;staphylococcus>
TTTGTACATTGAAAACTAGATAAGTAAGT <SEQ ID NO: 27;DNA;staphylococcus>
GCAAAACCGAGTGAATAAAGAGTTTTAAA <SEQ ID NO: 28;DNA;staphylococcus>
AAGCTTGAATTCATAAGAAATAATCGCTAG <SEQ ID NO: 29;DNA;staphylococcus>
AGCAAAACCGAGTGAATAAACAGTTTTAAA <SEQ ID NO: 30;DNA;staphylococcus>
ATTGTACATTGAAAACTAGATAAGTAAGTAA <SEQ ID NO: 31;DNA;staphylococcus>
AGTGTTCGAAAGAACACTCACAAGATTAATAA <SEQ ID NO: 32;DNA;staphylococcus>
AGCTTATTTAAAACTCTTTATTCACTCGGTTT <SEQ ID NO: 33;DNA;staphylococcus>
TAAAATAATGAAAACGAAGCCGTATGTGAGCGT <SEQ ID NO: 34;DNA;staphylococcus>
TAAAATAATGAAAACGAAGCCGTATGTGAGCGT <SEQ ID NO: 35;DNA;staphylococcus>
GAATTCATAAGAAATAATCGCTAGTGTTCGAAA <SEQ ID NO: 36;DNA;staphylococcus>
TTTCGAACACTAGCGATTATTTCTTATGAATTC -continued <SEQ ID NO: 37;DNA;*staphylococcus*>
GCAAAACCGAGTGAATAAAGAGTTTTAAATAAGC <SEQ ID NO: 38;DNA;*staphylococcus*>
GCTTATTTAAAACTCTTTATTCACTCGGTTTTGC <SEQ ID NO: 39;DNA;*staphylococcus*>
GCTTGGTAAAATCTATATTTTACTTACTTATCTAGT <SEQ ID NO: 40;DNA;*staphylococcus*>
GTACATTGAAAACTAGATAAGTAAGTAAAATATAGATT <SEQ ID NO: 41;DNA;*staphylococcus*>
GAGTTTTAAATAAGCTTGAATTCATAAGAAATAATCGC <SEQ ID NO: 42;DNA;*staphylococcus*>
GAAAGAACACTCACAAGATTAATAACGCGTTTAAATCTT <SEQ ID NO: 43;DNA;*staphylococcus*>
TTATAAAAGAACGTAACTTCATGTTAACGTTTGACTTATAA <SEQ ID NO: 44;DNA;*staphylococcus*>
TTATAAAAGAACGTAACTTCATGTTAACGTTTGACTTATAA <SEQ ID NO: 45;DNA;*staphylococcus*>
CTTCAGAAGATGCGGAA <SEQ ID NO: 46;DNA;*staphylococcus*>
TTTCGAACACTAGCGATT <SEQ ID NO: 47;DNA;*staphylococcus*>
GTTATTAAWCTTGTGAGTGTT <SEQ ID NO: 48;DNA;*staphylococcus*>
ACNMGTTATTAAWCTTGTGAG <SEQ ID NO: 49;DNA;*staphylococcus*>
CTTCAGAAGATGCGGAATA <SEQ ID NO: 50;DNA;*staphylococcus*>
TTCTTCAGAAGATGCGGAA <SEQ ID NO: 51;DNA;*staphylococcus*>
TTCTTTCGAACACTAGCGA <SEQ ID NO: 52;DNA;*staphylococcus*>
ACCAAGCAAAACCGAGTGAA <SEQ ID NO: 53;DNA;*staphylococcus*>
GTTCTTTCGAACACTAGCGA <SEQ ID NO: 54;DNA;*staphylococcus*>
NMGTTATTAAWCTTGTGAGTG <SEQ ID NO: 55;DNA;*staphylococcus*>
CGCGTTATTAATCTTGTGAG <SEQ ID NO: 56;DNA;*staphylococcus*>
CATTGAAMACTAGATAAGTA <SEQ ID NO: 57;DNA;*staphylococcus*>
GTTATTAAWCTTGTGAGTGTT <SEQ ID NO: 58;DNA;*staphylococcus*>
ACGCGTTATTAATCTTGTGAGT <SEQ ID NO: 59;DNA;*staphylococcus*>
CGAACACTAGCGATTATTTCTTA <SEQ ID NO: 60;DNA;*staphylococcus*>
ACTAGCGATTATTTCTTATGAAT <SEQ ID NO: 61;DNA;*staphylococcus*>
CATATTGTATTCAGTTTTGAATG <SEQ ID NO: 62;DNA;*staphylococcus*>
NMGTTATTAAWCTTGTGAG <SEQ ID NO: 63;DNA;*staphylococcus*>
CATATTGTATTCAGTTTTGAATGC <SEQ ID NO: 64;DNA;*staphylococcus*>
CATATTGTATTCAGTTTTGAATGT <SEQ ID NO: 65;DNA;*staphylococcus*>
CATAAGAAATAATCGCTAGTGTTCG <SEQ ID NO: 66;DNA;*staphylococcus*>
GACATATTGTATTCAGTTTTGAATG <SEQ ID NO: 67;DNA;*staphylococcus*>
GAAAACTAGATAAGTAAGTAAAATAT <SEQ ID NO: 68;DNA;*staphylococcus*>
TGTACATTGAAAACTAGATAAGTAAG <SEQ ID NO: 69;DNA;*staphylococcus*>
TTTGTACATTGAAMACTAGATAAG <SEQ ID NO: 70;DNA;*staphylococcus*>
ACNMGTTATTAAWCTTGTGAGTGTT

TABLE 2

| SEQ IDs NO | 62 (RP) | 57 (RP) | 59 (RP) | 46 (RP) | 60 (RP) | 53 (RP) | 51 (RP) | 54 (RP) | 55 (RP) | 58 (RP) |
|---|---|---|---|---|---|---|---|---|---|---|
| 52 (FP) | 1 | | | | | | | | | |
| 65 (FP) | | 2 | | | | | | | | |
| 45 (FP) | | | 3 | 4 | 5 | | | | | |
| 49 (FP) | | | 6 | 7 | 8 | | | | | |
| 50 (FP) | | | 9 | 10 | 11 | | | | | |
| 66 (FP) | 32 | | | | | 12 | 13 | 14 | 15 | 16 |
| 67 (FP) | | | | | | | | | 17 | 18 |
| 68 (FP) | 33 | | | | | | | | 19 | 20 |
| 63 (FP) | 21 | | | | | | | | 22 | 23 |
| 64 (FP) | 24 | | | | | | | | | |
| 61 (FP) | 25 | | 31 | | | 26 | | 27 | 28 | 29 |

FP/RP = Forward primers/Reverse primers

 = Preferred primer combinations

TABLE 3

| SEQ IDs NO | Hybprobe | Primercombination | Protocol PCR | Performance in the particular conditions of the examples |
|---|---|---|---|---|
| 24/33 | RStau63Fl.1/RStau65LC6.1(LCR640) | 1, 2 | $t°_a = 60°$ C. | + |
| 24/34 | RStau63Fl.1/RStau65LC7.1 (LCR705) | 1 | $t°_a = 60°$ C. | + |
| 42/43 | RStau73Fl.1/RStau75LC6.1 (LCR640) | 1, 2 | $t°_a = 60°$ C. | + |
| 42/44 | RStau73Fl.1/RStau75LC7.1 (LCR705) | 1 | $t°_a = 60°$ C. | + |
| 40/25 | RStauHP1-3Fl.1/RStauHP1-5LCR64.1 | 3, 4, 5, 6, 7, 8, 9, 10, 11, 27, 29, 31 | $t°_a = 55°$ C. | ++ |
| 37/35 | RStauHP2-3Fl.1/RStauHP2-LC6.1 | 12, 13, 15, 16, 17, 18, 19, 20, 22, 23, 28 | $t°_a = 55°$ C. | ++ |
| 36/38 | RStauHP2c-3Fl.1/RStauHP2c-LC6.1 | 14, 20, 33 | $t°_a = 55°$ C. | + |
| 41/31 | RStauHP3-3Fl.1/RStauHP3-LC6.1 | 14, 25, 33 | $t°_a = 55°$ C. | ++ |
| 26/14 | RStaphSP-3Fl.1/RStaphSP-5LC6.1 | 6, 12, 14, 21, 24, 25, 27, 29, 32 | $t°_a = 55°$ C. | + |
| 30/18 | RStauHP4.3Fl.1/RStauHP4-5LC6.1 | 29 | $t°_a = 55°$ C. | + |
| 15/21 | RStauHP5-Fl.1/RStauHP5a-5LC6.1 | 20 | $t°_a = 55°$ C. | + |
| 15/20 | RStauHP5-3Fl.1/RStauHP5b-5LC6.1 | 20 | $t°_a = 55°$ C. | + |
| 17/16 | RStauHP6-3Fl.1/RStauHP6a-5LC6.1 | 20 | $t°_a = 55°$ C. | + |
| 17/19 | RStauHP6-3Fl.1/RStauHP6b-5LC6.1 | 20 | $t°a = 50°$ C. | +++ |
| 27/28 | RStauHP7-3Fl/RStauHP7a-5LCR6 | 20 | $t°_a = 50°$ C. | + |
| 32/39/23 | RStauHP8.3Fl/RStauHP8.5LCR6/RStepHP8.5LCR6 | 29 | $t°_a = 55°$ C. | + |
| 29/22 | RStauHP9-3Fl/RStauHP9-5LC6 | 20 | $t°_a = 50°$ C. | + |

*The primer pairs in bold performed the best.

TABLE 4

*Staphylococci*

| Species (32) | Subspecies (15) | Clinical relevance | Coagulase reaction | Examined in this study |
|---|---|---|---|---|
| S. aureus | aureus | ++++ | + | + |
|  | anearobius | ++++ | + | + |
| S. epidermidis |  | +++ | – | + |
| S. capitis | capitis | + | – | + |
|  | ureolyticus | + | – | + |
| S. caprae |  | + | – | + |
| S. saccharolyticus |  | + | – | + |
| S. warneri |  | + | – | + |
| S. pasteuri |  | + | – | + |
| S. haemolyticus |  | +++ | – | + |
| S. hominis | hominis | + | – | + |
|  | novobiosepticum | + | – | – |
| S. lugdunensis |  | + | – | + |
| S. schleiferi | schleiferi | + | – | + |
|  | coagulans | + | + | + |
| S. muscae |  | – | – | – |
| S. auricularis |  | + | – | + |
| S. saprophyticus | saprophyticus | ++ | – | + |
|  | bovis | + | – | – |
| S. cohnii | cohnii | + | – | + |
|  | urealyticum | + | – | + |
| S. xylosus |  | – (+) | – | + |
| S. kloosii |  | – | – | – |
| S. equorum |  | – | – | – |
| S. arletae |  | – | – | – |
| S. gallinarum |  | – | – | – |
| S. simulans |  | + | – | + |
| S. carnosus |  | – | – | – |
| S. piscifermentans |  | – | – | – |
| S. felix |  | – | – | – |
| S. lutrae |  | – | + | – |
| S. intermedius |  | – | + | – |
| S. delphini |  | – | + | – |
| S. hyicus |  | – | (+) | + |
| S. chromogenes |  | – | – | + |
| S. sciuri | sciuri | – | – | + |
|  | carnaticus | – | – | – |
|  | rodentium | – | – | – |
| S. lentus |  | – | – | – |
| S. vitulus |  | – | – | – |

EXAMPLES

The method used in the examples is a method for the detection of Staphylococci, in particular *S. aureus, S. epidermidis* and *S. haemolyticus*, using the HybProbes of SEQ ID NO 17 and 19, in combination with a *Staphylococcus*-genus primer set of SEQ ID 58 and 68.

The HybProbes are labeled: SEQ ID NO 17 in 3' with fluorescein and SEQ ID NO 19 in 5' with LCred640.

In total, 63 *S. aureus* isolates (including one representative of the *S. aureus* subs. anaerobius), 48 *S. epidermidis* isolates and 16 *S. haemolyticus* isolates from different geographical origins were investigated.

If the isolates gave not the expected results, the gDNA was retyped by t-RNA PCR (Vaneechoutte, M. et al., 1998, Int. J. Syst. Bacteriol. (48) 127-139) and/or the culture was retyped by ApiSTAPH (Biomérieux).

The instrumentation is the LightCycler™ (version 1.2) provided with the adequate software (LC-software version 3.5) enabling a Real-Time fluorescence PCR detection.

Example 1

Preparation of the Samples to be Tested

1/. DNA from Pure Cultures

For extracting the DNA from pure cultures, different purification methods can be used:

Lysis with lysostaphin (5 µg/µl) for 1 h at 37° C. and purification with the QIAamp blood DNA isolation kit (Qiagen)

The method of Pitcher et al. (1989)

The MagNAPure LC DNA isolation Kit III (Bacteria, Fungi) on the MagNAPure instrument. Bacterial cells grown O/N on LB plates or slants were suspended in 100 to 1000 µl TE pH8 for storage at −20° C. 2 µl to 20 µl was used for extraction according to the manufacturer's recommendations.

QIAamp DNA mini kit (catalog no. 51306-QIAGEN). The culture was pre-treated enzymatically using lysozyme and lysostaphin.

2/. DNA from Positive Blood Culture Bottles

Blood samples were inoculated in aerobe blood culture bottles (BacT/ALERT FA) and incubated in a BacT/Alert 3D system (Organon Teknika) at 37° C. until positive. Positivity was monitored by a color change from dark green to yellow.

Aliquots (1.51 ml) of the blood cultures were frozen at −70° C. until use.

Genomic DNA was prepared as described in the pack insert of the MPLC DNA Isolation Kit III. As recommended for Organon Teknika blood culture bottles, prior to PCR the eluate was centrifuged 10 sec at 1400 rpm to spin down the extracted carbon particles.

Example 2

LightCycler (LC) Protocol

Following the instructions of the manufacturer of the kit LC-FastStart DNA Master Hybridization Probes (cat. No 3 003 243 or No 2 239 272):

any sample material suitable for PCR in terms of purity, concentration, and absence of inhibitors can be used;

the primers should be at a final concentration of 0.3 to 1 µM each;

the HybProbes at a final concentration of 0.2 µM each, or double;

the concentration of $MgCl_2$ should be optimized, and may vary from 1 to 5 mM;

and a negative control should be run.

The amplification and melting conditions are described herein after. The LC software version 3.5 was used. The quantification settings were F2/back F1 (samples). For the baseline adjustment the arithmetic mode was used. The crossing point (Ct) calculation was based on the second derivative maximum. The calculation method for the melting peak was polynomial. The peak area was used to calculate the Tm.

Amplification and Melting Curve Program:

|  |  | Temp. (° C.) | Hold time | Slope (° C./sec.) | Acquisition mode |
|---|---|---|---|---|---|
|  | Denaturation | 95 | 10 min | 20 | None |
| 45x | Cycles | 95 | 10 sec | 20 | None |
|  |  | 50 | 15 sec | 20 | SINGLE |
|  |  | 72 | 10 sec | 20 | None |
|  | Melting | 95 | 60 sec | 20 | None |
|  |  | 40 | 60 sec | 20 | None |
|  |  | 80 | 0 sec | 0.1 | CONTINUOUS |
|  | Cooling | 40 | 0 sec | 20 | None |

Example 3

Results on Purified DNA, Inclusivity and Cross Reactivity Tests

1/ Inclusivity

All S. aureus isolates examined (n=63) were successfully amplified (Ct range 17.25-33.51) and gave one uniform melting peak with a mean Tm of 53.13° C.±0.52° C. whatever the geographical or specimen origin.

It has to be noted that the subspecies S. aureus subs. anaerobius fell together with the S. aureus species.

All isolates received as S. epidermidis (n=48) and S. haemolyticus (n=16) could be detected using the melting curve. Quantification curves usually were not observed. The average Tm value for S. epidermidis isolates was 44.55° C.±0.21° C. and for S. haemolyticus isolates it was 44.96° C.±0.24° C. There were no differences observed among isolates from different geographical or specimen origin.

All isolates received as S. aureus or S. haemolyticus reacted as expected. However, deviating results were obtained for five S. epidermidis isolates.

Two of these, one from UK and one from Italy, were afterwards identified as S. hominis. Another S. epidermidis isolate from UK showed a Tm value of 49.02° C. and could afterwards only be determined as a Staphylococcus species (not S. aureus, S. epidermidis or S. haemolyticus). The UK isolate was afterwards retyped as a S. haemolyticus. And one isolate from Spain producing an uncharacteristic small melting peak was retyped as S. intermedius or S. chromogenes.

2/. Cross-Reactivity

More than 50 different bacterial species were tested (Mycobacteria, Pseudomonas, Streptococci, etc) and also few fungi. None of the tested organisms generated quantification curves or melting peaks with the assay.

3/. Conclusion:

All S. aureus isolates investigated are detected (100% sensitivity) and could be unequivocally distinguished from all other isolates studied.

Also for S. epidermidis and S. haemolyticus the sensitivity was 100%.

Therefore using this particular set of HybProbes of SEQ IDs NO 17 and 19, both species are detected without being differentiated from each other or from other CoNS.

Unwanted cross-reactivities, with organisms from the pathogens tested were not observed.

Summary of the Sensitivity and Specificity Tests.

|  |  | # of strains with | | |
|---|---|---|---|---|
| Taxon | # of strains tested | Peak at 53° C. | Peak below 49° C. | No peak |
| S. aureus | 63 | 63 | 0 | 0 |
| S. epidermidis | 43 | 0 | 43 | 0 |
| S. haemolyticus | 16 | 0 | 16 | 0 |
| Cross-check list | 55 | 0 | 0 | 55 |
| Human DNA | 1 | 0 | 0 | 1 |

Example 4

Results on Blood Cultures

In total aliquots of 16 positive blood culture bottles inoculated with patient-samples were tested.

From the five bottles that grew *S. aureus,* 4 could be identified as such. One showed no peak. Indeed, the DNA of the sample was retyped as *S. schleiferi.*

Out of the ten bottles found positive for *S. epidermidis,* 7 showed a peak at 44-45° C.—as expected—while three showed peaks shifted to 47° C. After retyping the DNA of the deviating samples, they were identified as *S. hominis.*

One bottle, positive for *S. haemolyticus,* produced the expected melting peak at 44.59° C.

Example 5

Detection of Other

In total 51 CoNS-strains, other than *S. epidermidis* and *S. haemolyticus,* have been studied. The results are summarized in the table below.

Amplification was observed on gel for all stains of all species except two (*S. schleiferi* and *S. sciuri*) for which the results are ambiguous (see also below). Some CoNS produced a growth curve (amplification), with corresponding Ct value, but the endpoint fluorescence was very low (0.004 or less) as compared to the values obtained for *S. aureus* (e.g. 0.03 for $10^3$ copies).

Most species examined were detectable by melting curve analysis, with the exception of *S. chromogenes, S. hyicus* and *S. simulans.*

The results for *S. schleiferi* and *S. sciuri* are obscure; for both species melting peaks were observed but could not be discriminated with certainty from a potential contaminating agent. Results obtained with universal primers suggest that both species will presumably not be detectable; there was clear prove of amplification on gel, but the HybProbes did not generate a signal in the LC.

The Tm range observed for CoNS is 39 to 48° C. This is clearly different from that of *S. aureus* but perfectly overlapping the range of *S. epidermidis* and *S. haemolyticus.*

Summary of the LC results obtained for strains of the *Staphylococcus* species examined.

| Species | # strains tested | Amplicon on gel (+/−140 bp) | Ct detection | Range Tm (° C.) melting peak | Melting peak detection |
| --- | --- | --- | --- | --- | --- |
| *S. aureus* | 70 | + | Yes | 52-54 | Yes |
| *S. epidermidis* | 12 | + | No | 43-45 | Yes |
| *S. haemolyticus* | 21 | + | No | 44-46 (47) | Yes |
| *S. auricularis* | 3 | + | No | 39-40 | (Yes) |
| *S. capitis* | 4 | + | No | 46-47 | Yes |
| *S. caprae* | 2 | + | No | 45-46 | Yes |
| *S. chromogenes* | 1 | + | No | — | No |
| *S. cohnii* | 3 | + | (Yes) | 46-48 | Yes |
| *S. hominis* | 6 | + | No | 46-48 | Yes |
| *S. hyicus* | 1 | + | No | — | No |
| *S. lugdunensis* | 12 | + | (Yes) | 46-48 | Yes |
| *S. pasteuri* | 1 | + | (Yes) | 47 | Yes |
| *S. saccharolyticus* | 1 | + | No | 45 | Yes |
| *S. saprophyticus* | 5 | + | No | 42-43 | Yes |
| *S. schleiferi* | 4 | ? | No | ? | ? |
| *S. sciuri* | 1 | ? | No | ? | ? |
| *S. simulans* | 1 | + | No | — | No |
| *S. warneri* | 5 | + | (Yes) | (42) 46-47 | Yes |
| *S. xylosus* | 1 | + | No | 42 | Yes |
| Total | 154 | | | | |

We claim:

1. A method for the detection and/or identification of *Staphylococcus aureus* in a sample, comprising the steps of
   (i) hybridizing the polynucleic acids of the sample with at least two polynucleotide probes that hybridize to a target sequence within 25 nucleotides of each other, wherein the at least two polynucleotide probes are SEQ ID NO:17 and SEQ ID NO:19, and wherein the target sequence comprises at least 50 consecutive nucleotides from a nucleic acid molecule of
   SEQ ID NO:1 or
   SEQ ID NO: 2 or
   a *Staphylococcus aureus* sequence homologous to SEQ ID NO:1, or
   a *Staphylococcus aureus* sequence homologous to SEQ ID NO: 2, or
   the RNA form of SEQ ID NO: 1 wherein T is replaced by U, or
   the RNA form of SEQ ID NO 2 wherein T is replaced by U, or
   the RNA form of said *Staphylococcus aureus* specific homologue of SEQ ID NO: 1 wherein T is replaced by U, or
   the RNA form of said *Staphylococcus aureus* specific homologue of SEQ ID NO: 2 wherein T is replaced by U, or
   the sequence complementary to SEQ ID NO:1
   the sequence complementary to SEQ ID NO:2
   the sequence complementary to the *Staphylococcus aureus* sequence homologous to SEQ ID NO:1, or
   the sequence complementary to the *Staphylococcus aureus* sequence homologous to SEQ ID NO:2, or
   the sequence complementary to the RNA form of said SEQ ID NO:1 wherein T is replaced by U, or
   the sequence complementary to the RNA form of said SEQ ID NO:2 wherein T is replaced by U, or
   the sequence complementary to the RNA form of said *Staphylococcus aureus* sequence homologous to SEQ ID NO: 1 wherein T is replaced by U,
   the sequence complementary to the RNA form of said *Staphylococcus aureus* sequence homologous to SEQ ID NO:2 wherein T is replaced by U,
   (ii) detecting the hybrids formed as a result of (i), and
   (iii) detecting or identifying *Staphylococcus aureus* in the sample based on the presence of the hybrids detected in (ii)
   wherein the method comprises the step of amplifying the 16S-23S rRNA spacer region, or a fragment comprising the target sequence, or the target sequence in a PCR amplification preceding step (i),
   wherein the PCR amplification comprises the use of the primers of SEQ ID NO:68 and SEQ ID NO:58.

2. A method according to claim 1, wherein the method comprises the step of releasing, isolating and/or concentrating the polynucleic acids in the sample preceding the PCR amplification.

* * * * *